(12) United States Patent
Baek et al.

(10) Patent No.: US 7,211,606 B2
(45) Date of Patent: May 1, 2007

(54) PROCESS FOR THE PREPARATION OF DIMETHYLETHER FROM HYDROCARBONS

(75) Inventors: Young Soon Baek, Incheon (KR); Won Ihl Cho, Uijeongbu-si (KR); Byoung Hak Cho, Incheon (KR); Jung Chul Suh, Seoul (KR); Dong Hyuk Kim, Incheon (KR); Hyung Gyu Kim, Incheon (KR); Seung Ho Lee, Incheon (KR); Woo Sung Ju, Goyang-si (KR)

(73) Assignee: Kores Gas Corporation, Gyeonggi-do (KR)

( * ) Notice: Subject to any disclaimer, the term of this patent is extended or adjusted under 35 U.S.C. 154(b) by 0 days.

(21) Appl. No.: 11/450,580

(22) Filed: Jun. 10, 2006

(65) Prior Publication Data

US 2006/0287405 A1    Dec. 21, 2006

(30) Foreign Application Priority Data

Jun. 17, 2005  (KR) .................. 10-2005-0052564
May 23, 2006  (KR) .................. 10-2006-0046112

(51) Int. Cl.
*C07C 27/00* (2006.01)
(52) U.S. Cl. .................. 518/700; 518/702; 518/703; 518/704; 518/713; 518/714; 518/715
(58) Field of Classification Search ............... 518/700, 518/702–704, 713, 714, 715
See application file for complete search history.

(56) References Cited

U.S. PATENT DOCUMENTS 6,800,665 B1 * 10/2004 Shikada et al. ............. 518/713

* cited by examiner

*Primary Examiner*—J. Parsa
(74) *Attorney, Agent, or Firm*—Abelman, Frayne & Schwab

(57) ABSTRACT

Disclosed herein is a process for the preparation of dimethylether from hydrocarbons, including tri-reforming a feedstock mixture comprised of hydrocarbons, carbon dioxide and water vapor in the presence of a tri-reforming catalyst, to prepare a syngas, which then undergoes gas-phase direct synthesis into dimethylether in one step in the presence of a hybrid catalyst. According to the process of this invention, three main processes among typical syngas preparation processes are simultaneously performed, and then, the syngas thus obtained is prepared into dimethylether through a direct reaction in one step, thereby decreasing the apparatus cost and operation cost. In addition, all of the carbon dioxide separated and recovered from the unreacted material and by-products may be reused as reaction material, thus decreasing the generation of carbon dioxide and reducing the material cost.

9 Claims, 1 Drawing Sheet

PROCESS FOR THE PREPARATION OF DIMETHYLETHER FROM HYDROCARBONS

BACKGROUND OF THE INVENTION

1. Field of the Invention

The present invention relates, generally, to a process for the preparation of dimethylether (DME) from hydrocarbons, and, more particularly, to a process for the preparation of DME from hydrocarbons through a tri-reforming reaction and a gas-phase DME direct synthesis reaction over special catalysts in one step.

2. Description of the Related Art

Recently, DME, which has LPG-like physical properties and other excellent properties, is receiving attention as an aerosol propellant, a substitute material for diesel fuel, LPG, LPG-mixed fuel and an intermediate of chemical reactions.

In general, a process for the preparation of DME from hydrocarbons includes reforming hydrocarbons, serving as a reaction material, through a plurality of reaction procedures to synthesize a syngas, and then subjecting the syngas, serving as a reaction material, to methanol synthesis and methanol dehydration to obtain DME.

As such, the synthesis of the syngas is realized through the following three processes.

In a first process, a hydrocarbon (e.g., methane) and water vapor are catalytically reacted at about 800–900° C., to be converted into hydrogen and carbon monoxide. The production of hydrogen and carbon monoxide is conducted at a high temperature in the presence of a nickel catalyst through Reaction 1 below, and thus, hydrogen and carbon monoxide are produced at a molar ratio of 3:1:

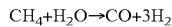

$$CH_4 + H_2O \rightarrow CO + 3H_2 \qquad \text{Reaction 1}$$

The process using the above reaction, which was first introduced by BASF GmbH, Germany, in 1926, has been internationally popularized, and therefore, industrial foundations for thermodynamic research, catalysts, and reaction conditions have been based thereon. In the reforming reaction, having the goals of prevention of back reactions and inhibition of coking of a catalyst, water vapor is supplied in an amount three times greater than the reaction material, and the reaction temperature is maintained at 600–900° C.

In a second process, methane gas and oxygen are reacted at a high temperature to induce the combustion reaction. At this time, the temperature required for the reaction is maintained using the combustion heat generated.

In a third process, carbon dioxide and methane gas are reacted to produce hydrogen and carbon monoxide, which is referred to as $CO_2$ dry reforming. Since this process is an endothermic reaction, it functions to decrease the temperature of the reactor. Hence, the reaction temperature has to be maintained using the combustion heat obtained in the second process.

The syngas thus obtained is synthesized into methanol using a methanol synthesis catalyst, after which methanol is transformed into DME as a final product using a methanol dehydration catalyst.

That is, the conventional DME production process is disadvantageous because at least two reaction procedures, including the conversion of syngas into methanol and the conversion of methanol into DME, should be conducted.

According to the conventional techniques, since the synthesis of the syngas from hydrocarbons and the synthesis of DME from the syngas each require at least two reaction procedures, a plurality of reactors must be operated. As such, a problem exists in that all of the reactions must be stopped if one reaction is stopped. In addition, expensive apparatus is required and high operating costs are incurred, due to the use of a plurality of reactors.

As well, carbon dioxide, generated in individual synthesis procedures, is released into the atmosphere, thus contributing to the greenhouse effect.

SUMMARY OF THE INVENTION

Leading to the present invention, the intensive and thorough research on production of DME, carried out by the present inventors aiming to avoid the problems encountered in the prior arts, resulted in the finding that a specific catalyst may be used, whereby the total number of reaction steps is drastically decreased, thus preparing DME through an economical and efficient process.

Accordingly, it is an object of the present invention to provide a process of economically and efficiently preparing DME, which comprises reforming hydrocarbons in one step, to synthesize a syngas, which then undergoes gas-phase DME direct synthesis in one step.

It is another object of the present invention to provide a process of preparing DME from hydrocarbons, in which carbon dioxide generated from each process is separated, recovered, and reused as a reaction material, thereby remarkably decreasing the generation of carbon dioxide.

In order to accomplish the above objects, the present invention provides a process for the preparation of DME from hydrocarbons, comprising the following steps of:

(a) simultaneously subjecting a feedstock mixture including C1–C4 hydrocarbons, carbon dioxide and water vapor, and an oxidant, to $CO_2$ dry reforming and steam reforming, in the presence of a tri-reforming catalyst, to obtain a reaction product gas mixture comprising hydrogen, carbon monoxide, unreacted material, and by-products, This technique can be controlled by reactant composition to obtain desirable $H_2/CO$ ratio;

(b) separating and recovering the unreacted material and by-products including carbon dioxide from the reaction product gas mixture obtained in step (a), to obtain a syngas including hydrogen and carbon monoxide;

(c) simultaneously subjecting the syngas to methanol synthesis and methanol dehydration in the presence of a hybrid catalyst, to obtain a reaction product gas mixture including DME, unreacted material and by-products; and (d) separating and recovering the unreacted material and by-products including carbon dioxide from the reaction product gas mixture obtained in step (c), to obtain DME, wherein said tri-reforming catalyst comprises Ni/Ce/$ZrO_2$/MgO/Cr/$\gamma$-$Al_2O_3$, and said hybrid catalyst comprises a methanol synthesis catalyst including Cu/Zn/Zr/Al/Mn/Ga, a methanol dehydration catalyst including $\gamma$-$Al_2O_3$, and a binding material having an average particle size of 10–100 nm, which are physically combined together.

The above process may further comprise methanation cracking a feedstock including C1–C4 hydrocarbons and carbon dioxide, and water vapor, to obtain a feedstock mixture, before step (a).

In addition, the using amount of (i) C1–C4 hydrocarbons, (ii) carbon dioxide, and (iii) water vapor, in the feedstock mixture, and (iv) oxidant are (i) 22.94–38.17 vol %, (ii) 29.01–35.78 vol %, (iii) 9.54–17.65 vol %, and (iv) 20.35–23.85 vol %, respectively.

The tri-reforming catalyst may comprise 14.03–17.32 wt % Ni, 1.16–1.43 wt % Ce, 6.93–8.55 wt % $ZrO_2$, 16.36–20.20 wt % MgO, 20.05–24.75 wt % Cr, and 31.47–38.85 wt % $\gamma$-$Al_2O_3$.

The binding material may be any one selected from the group consisting of carbon black, graphite, pitch and coal tar.

The syngas may comprise $H_2$ and CO at a volune ratio of 0.5–3.0:1.

Further, step (a) is preferably performed at 900–1200° C., and step (c) is preferably performed at 150–400° C. under pressure of 20–350 kg/cm².

In addition, the carbon dioxide separated in steps (b) and (d) may be recovered, respectively, to be reused as feedstock in step (a).

BRIEF DESCRIPTION OF THE DRAWING

The above and other objects, features and advantages of the present invention will be more clearly understood from the following detailed description taken in conjunction with the accompanying drawing, in which.

DESCRIPTION OF THE PREFERRED EMBODIMENTS

Figure 1:
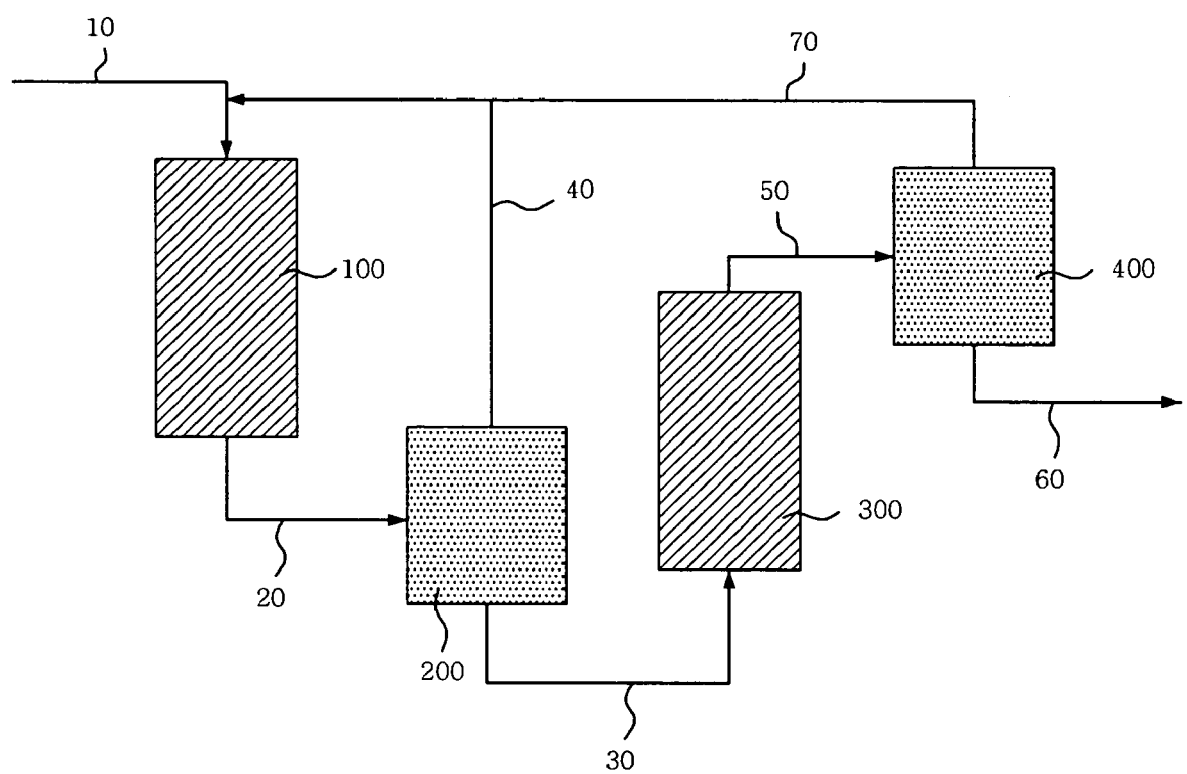
FIG. 1 is a view showing the process of preparing DME using hydrocarbons as a reaction material, according to the present invention.

Hereinafter, a detailed description will be given of the present invention, with reference to the appended drawing.

FIG. 1 is a view showing the process of preparing DME using hydrocarbons as a reaction material, according to the present invention.

According to the preparation process of the present invention, before a feedstock mixture comprising C1–C4 hydrocarbons, carbon dioxide and water vapor is supplied into a tri-reformer 100 serving as a syngas preparation reactor to tri-reform it, a methanation cracking reaction may be performed as a pretreatment procedure.

That is, a feedstock including C1–C4 hydrocarbons and carbon dioxide is loaded along with water vapor into a typical methanizing cracker, to crack C1–C4 hydrocarbons to obtain methane, thus obtaining a feedstock mixture.

The feedstock includes C1–C4 hydrocarbons, such as natural gas, propane gas, butane gas, naphtha, or mixtures thereof, and carbon dioxide. In addition, as the feedstock, a crude material containing carbon dioxide, which is directly supplied from a gas well, may be used.

As such, the cracking reaction is typically conducted at 250–400° C. under pressure ranging from atmospheric pressure to 50 kg/cm².

Through the cracking reaction from C1–C4 hydrocarbons into methane as a C1 hydrocarbon, liquefied petroleum gases or naphtha having large carbon numbers are catalytically reformed so that the methane gas has a concentration of 90 vol % or more, and preferably, 99 vol % or more, with the balance being a feedstock mixture including hydrogen, carbon dioxide, carbon monoxide and unreactive water vapor.

The above methanation cracking reaction is applied to methods of preparing substitute natural gas (SNG), composed mainly of methane, from propane or naphtha, in the presence of a nickel catalyst.

In producing a syngas composed mainly of carbon monoxide and hydrogen, although carbons are deposited on a catalyst when catalytic reforming of natural gas is conducted, when catalytic reforming of hydrocarbons having 3 or more carbons, such as propane, butane and naphtha, is conducted using water vapor, carbons are deposited on the catalyst more easily, compared to the catalytic reforming of natural gas having one carbon into a gaseous state. Thus, in the present invention, the methanation cracking reaction may, if desired, be conducted before the main reforming process to reduce the amount of deposited carbons.

Thereafter, as the main reforming process of the present invention, a reaction mixture 10 including a feedstock mixture comprised of a hydrocarbon (preferably, methane), carbon dioxide and water vapor, which are obtained through the above pretreatment or directly supplied without having been pretreated, and an oxidant is supplied into the tri-reformer 100 in the presence of a tri-reforming catalyst, followed by simultaneously performing $CO_2$ dry reforming and steam reforming, thus obtaining a reaction product gas mixture 20 including hydrogen, carbon monoxide, unreacted material and by-products.

Preferably, while the feedstock mixture and the oxidant are passed through a burner (not shown) provided in the upper portion of the tri-reformer 100, they are converted into a hot reactive gas through the combustion of oxygen and methane gas. As such, the reaction temperature is maintained at a predetermined level, due to the hot reactive gas.

Further, it is preferable that the burner (not shown) be maintained at 1200–1400° C., and that the inside of the tri-reformer 100 be maintained at 900–1200° C. If the temperature of the burner (not shown) is less than 1200° C., it is difficult to maintain the internal temperature of the tri-reformer, and carbon cokings are present in a large amount. Meanwhile, if the above temperature exceeds 1400° C., the nozzle of the burner, the burner and the main body of the reformer must be equipped with additional apparatus, due to the high temperature, thus generating additional apparatus cost. Further, if the internal temperature of the tri-reformer 100 is less than 900° C., cokes are present in a large amount due to a side reaction. Meanwhile, if the above temperature exceeds 1200° C., the reaction temperature is difficult to control, and the lifetime of the tri-reforming catalyst is shortened.

Preferably, the tri-reforming reaction is conducted at a pressure from 5 to 40 kg/cm²g. If the pressure is less than 5 kg/cm²g, unreacted methane remains in a large amount, and less carbon monoxide is formed. On the other hand, if the pressure exceeds 40 kg/cm²g, hydrogen backfire may occur.

The oxidant is selected from among pure oxygen, a mixture of oxygen and nitrogen, a mixture of oxygen and carbon dioxide, and a mixture of oxygen and an inert gas.

When supplying the feedstock mixture, including C1–C4 hydrocarbons, carbon dioxide and water vapor, together with the oxidant, 22.94–38.17 vol % C1–C4 hydrocarbons, 29.01–35.78 vol % carbon dioxide, 9.54–17.65 vol % water vapor, and 20.35–23.85 vol % oxidant are preferably used. When any component of feedstock or oxidant is used outside of its respective range as given above, the component ratio of the prepared syngas, that is, the ratio of hydrogen to carbon monoxide, falls outside of 0.8–1.2:1. Moreover, carbon cokings may be present in a large amount due to a side reaction, and also, the reaction temperature is difficult to control.

The hot reactive gas simultaneously undergoes a carbon dioxide reforming reaction and a steam reforming reaction while passing over the tri-reforming catalyst bed included in the tri-reformer 100, the tri-reforming catalyst of which consists of Ni, Ce, $ZrO_2$, MgO, Cr and $\gamma$-$Al_2O_3$.

Preferably, the tri-reforming catalyst comprises 14.03–17.32 wt % Ni, 1.16–1.43 wt % Ce, 6.93–8.55 wt % $ZrO_2$, 16.36–20.20 wt % MgO, 20.05–24.75 wt % Cr, and 31.47–38.85 wt % $\gamma\text{-}Al_{23}$.

When the tri-reforming catalyst of the present invention, having the above composition and composition ratio, is used, a desired syngas can be prepared and large carbon cokes are present in a somewhat decreased amount. In addition, where a conventional catalyst prepared using expensive precious metal (Pd, Pt, etc.) increases the process cost, resulting in negated economic benefits, the catalyst of the present invention is formed of an inexpensive material, thereby reducing the process cost.

According to a preferred embodiment, in the above catalyst, for example, γ-alumina ($\gamma\text{-}Al_2O_3$), serving as a support, is suspended in an aqueous solution of metal(Ni, Ce, Zr, Mg, Cr, etc.) nitrate in a predetermined amount to prepare a catalyst slurry, and the catalyst slurry is dried. The dried slurry communicates with a flask containing the mixture to be lowered to a low pressure of 100 Torr, and water is evaporated therefrom at 80° C. The catalyst precursor powder obtained by evaporating water is, then, loaded into a dry oven, dried at 100° C. for 12 hr, loaded into a burning furnace, and burned at 450° C. for 3 hr in air, thus obtaining a desired metal oxide type catalyst, to which the present invention is, however, not limited.

Subsequently, the reaction product gas mixture 20 is supplied into a syngas separator 200 in the next stage, so that the unreacted material and by-products including carbon dioxide 40 may be separated from the reaction product gas mixture 20, thus separating and recovering a syngas 30 including hydrogen and carbon monoxide.

The separation and recovery processes of the syngas are not particularly limited in the present invention, as long as they are known in the art.

In the syngas obtained through the separation, when hydrogen and carbon monoxide are present at a volume ratio of about 0.5–3.0:1, and preferably, 0.8–1.2:1, the best syngas composition for synthesis of DME is obtained, thus increasing the DME productivity.

The carbon dioxide 40 and the methane gas recovered through the separation are recycled to be reused as feedstock for the tri-reforming reaction.

Then, the syngas 30 is supplied into a DME synthesis reactor 300 in the next stage and then simultaneously undergoes methanol synthesis and methanol dehydration in the presence of a hybrid catalyst, thus obtaining a reaction product gas mixture 50 including DME, unreacted material and by-products.

As such, the hybrid catalyst must be very efficient for the effective conversion of the syngas into methanol, and also act to accelerate the dehydration of methanol. Further, the methanol synthesis and methanol dehydration must result in a high conversion rate; high selectivity, and low deactivation. That is, the hybrid catalyst used in the present invention should have both an active point for methanol synthesis and an active point for methanol dehydration.

To provide a hybrid catalyst meeting the above conditions, Cu, Zn, Zr, Al, Mn and Ga salts are coprecipitated, preparing a methanol synthesis catalyst. Preferably, the coprecipitation is conducted under conditions of 80° C., pH 6–9, and a stirring rate of 300–600 rpm, but the present invention is not limited thereto.

The ratio by weight of Cu, Zn, Zr, Al, Mn and Ga of the methanol synthesis catalyst composition is preferably 22.6–67.8:13.5–40.6:2.3–6.7:10.4–31.2:3.8–7.5:0.9–2.7, to realize combination between a methanol synthesis catalyst and a methanol dehydration catalyst, and a water gas conversion reaction.

Although the particle size of the methanol synthesis catalyst is not particularly limited, this catalyst is preferably pulverized to have an average particle size ranging from about 10 to 100 μm.

Separately, $\gamma\text{-}Al_2O_3$ is heat treated at 180–360° C., to prepare a methanol dehydration catalyst. The heat treatment is preferably conducted under the above conditions, to remove lubricants or unnecessary components remaining in pores of the catalyst upon preparation of $\gamma\text{-}Al_2O_3$.

Although the particle size of the methanol dehydration catalyst is not particularly limited, this catalyst is preferably pulverized to have an average particle size ranging from about 10 to 100 μm.

Finally, the methanol synthesis catalyst and the methanol dehydration catalyst thus obtained are physically combined with a binding material having an average particle size of about 10–100 nm, thereby preparing the hybrid catalyst of the present invention.

The binding material is any one selected from the group consisting of carbon black, graphite, pitch, and coal tar.

The binding material has an average particle size ranging from 10 to 100 nm, and preferably, from 20 to 30 nm, to be suitable for the physical combination of catalysts different from each other.

The methanol synthesis catalyst, the methanol dehydration catalyst and the binding material of the hybrid catalyst are used at the ratio of 40–79 wt %: 20–50 wt %: 1–10 wt %, but the present invention is not limited thereto.

Further, it is most preferable that the methanol direct synthesis conducted in the presence of the hybrid catalyst be performed at 150–400° C. under pressure of about 20–350 $kg/cm^2$, in view of economical and reaction efficiencies.

In addition, the above reaction may be performed using a gaseous fixed-bed reactor or a fluidized-bed reactor. In the case where the reaction is conducted using the fluidized-bed reactor, it is most preferable to carry out the reaction at a rate of 1,000–10,000 $hr^{-1}$, in view of process efficiency.

Subsequently, the obtained reaction product gas mixture 50 is supplied into a DME separator 400 in the next stage, to separate the unreacted material and by-products containing carbon dioxide 70 from hydrogen and DME 60, after which the DME 60 is recovered.

The separation and recovery processes of DME are not particularly limited as long as they are known in the art.

Carbon dioxide 70, recovered upon separation, is mixed with the reactant stream 10 for the preparation of a syngas, and is then re-supplied into the tri-reformer 100.

A better understanding of the present invention may be explained in detail as the following example which is set forth to illustrate, but is not to be construed to limit the present invention.

EXAMPLE 1

A feedstock supplied from a gas well, including natural gas (C, 91.35 vol %), C2 (6.66 vol %), C3 (3.04 vol %), C4 (1.48 vol %), C5 (0.05 vol %), and carbon dioxide, and preheated water vapor were supplied into a methanizing cracker to perform a cracking reaction at about 300° C. under atmospheric pressure.

A feedstock mixture obtained through the cracking reaction was supplied into a tri-reformer in the next stage while injecting oxygen gas into the upper portion of the tri-reformer. The temperature of a burner, provided in the upper portion of the tri-reformer into which the feedstock mixture and the oxidant were supplied, was controlled to about 1200° C., to cause the combustion of methane and oxygen gas among the supplied gases. Through the combustion, the supplied gases were converted into a hot reactive gas, so that the reaction temperature was maintained at about 1000° C., and the reaction pressure was controlled to 10 kg/cm²g, causing the tri-reforming reaction.

As such, the natural gas, carbon dioxide, and water vapor in the feedstock, and the oxidant, were supplied at the ratio of 35:32:11:22 (vol %).

The reaction product gas mixture obtained through the tri-reforming reaction was cooled while passing through a cooler in the next stage, after which the cooled gas mixture was supplied into a gas-liquid separator to collect a liquid product, such as unreacted material and/or by-products, using a drain, and collect syngas using a syngas outlet.

Then, carbon dioxide and methane gas were separated and recovered from the collected syngas, and thus, recycled into the first process to be reused as the feedstock mixture, while the remaining syngas components were supplied into a DME synthesis reactor including a hybrid catalyst in the next stage, to conduct a DME synthesis reaction. As such, this DME synthesis reaction was conducted at 320° C. and 30 kg/cm².

The reaction product gas mixture thus obtained was separated and recovered according to a typical process, thus obtaining DME. At this time, the separated and recovered carbon dioxide was recycled into the first process, to be reused as feedstock.

The conversion rate, selectivity and productivity of DME prepared through the tri-reforming reaction of hydrocarbons and DME synthesis were measured. The results are shown in Table 1 below.

As such, the catalyst for use in the tri-reforming reaction was composed of 16.5 wt % Ni, 1.2 wt % Ce, 7.3 wt % $ZrO_2$, 18 wt % MgO and 22 wt % Cr supported to γ-alumina (35 wt %).

In addition, the hybrid catalyst for use in DME direct synthesis was prepared by separately preparing a synthesis catalyst and a dehydration catalyst, and adding carbon black to the above two catalysts to physically combine them.

(a) To prepare the methanol synthesis catalyst, the following metal hydrides were used. That is, 39.8 wt % $Cu(NO_3)_2 \cdot 3H_2O$, 35.7 wt % $Zn(NO_3)_2 \cdot 6H_2O$, 14.5 wt % $Al(NO_3)_3 \cdot 9H_2O$, 4.7 wt % $Zr(NO_3)_3 \cdot 9H_2O$, 3.8 wt % $Mn(NO3)_2$, and 1.5 wt % $Ga(NO_3)_3 \cdot 6H_2O$ were added to distilled water to obtain an aqueous solution. Then, 100 wt % $Na_2CO_3 \cdot 10H_2O$ was made into an aqueous solution to be used as a precipitant. The precipitate thus obtained was washed several times with distilled water, after which water was removed. The precipitates were dried at 80–120° C. and then burned at 220–500° C. The dried precipitates were pulverized to a small size of 20–100 μm, thereby preparing a methanol synthesis catalyst of the present invention.

(b) γ-alumina was heat treated at about 180–360° C. for 12 hr, and was thus used as a methanol dehydration catalyst.

(c) The methanol synthesis catalyst obtained in (a) and the dehydration catalyst obtained in (b) were pulverized, and filtered using a sieve having 400–635 meshes. Thereafter, 75 wt % methanol synthesis catalyst and 21 wt % dehydration catalyst were mixed with 4 wt % carbon black to physically combine them, resulting in a hybrid catalyst.

TABLE 1

| | Conversion (%) | Selectivity (%) | Productivity (g-mol/Kg-cat · hr) |
|---|---|---|---|
| Ex. 1 | 37.50 | 70.96 | 13.18 |

Although the preferred embodiment for preparation of DME from hydrocarbons of the present invention has been disclosed for illustrative purposes, those skilled in the art will appreciate that various modifications, additions and substitutions are possible, without departing from the scope and spirit of the invention as disclosed in the accompanying claims.

As described above, the present invention provides a process for the preparation of DME from hydrocarbons. According to the present invention, three main processes among typical syngas preparation processes are simultaneously performed, and then, the syngas thus obtained undergoes a direct reaction in one step to prepare DME, thereby decreasing the apparatus cost and operation cost.

In addition, carbon dioxide generated upon the synthesis of syngas and of DME is separated and recovered, after which all of the recovered carbon dioxide may be reused, thus decreasing the generation of carbon dioxide and reducing the material cost.

What is claimed is:

1. A process for the preparation of dimethylether from hydrocarbons, comprising the following steps of:
   (a) simultaneously subjecting a feedstock mixture including C1–C4 hydrocarbons, carbon dioxide, and water vapor, and an oxidant, to $CO_2$ dry reforming and steam reforming, in the presence of a tri-reforming catalyst, to obtain a reaction product gas mixture comprising hydrogen, carbon monoxide, unreacted material, and by-products;
   (b) separating and recovering the unreacted material and by-products including carbon dioxide from the reaction product gas mixture obtained in step (a), to obtain a syngas including hydrogen and carbon monoxide;
   (c) simultaneously subjecting the syngas to methanol synthesis and methanol dehydration in the presence of a hybrid catalyst, to obtain a reaction product gas mixture including dimethylether, unreacted material and by-products; and
   (d) separating and recovering the unreacted material and by-products including carbon dioxide from the reaction product gas mixture obtained in step (c), to obtain dimethylether,
   wherein said tri-reforming catalyst comprises Ni/Ce/$ZrO_2$/MgO/Cr/γ-$Al_2O_3$, and
   said hybrid catalyst comprises a methanol synthesis catalyst including Cu/Zn/Zr/Al/Mn/Ga, a methanol dehydration catalyst including γ-$Al_2O_3$, and a binding material having an average particle size of 10–100 nm, which are physically combined together.

2. The process as set forth in claim 1, further comprising methanation cracking a feedstock, including C1–C4 light hydrocarbons and carbon dioxide, and water vapor, to obtain a feedstock mixture, before step (a).

3. The process as set forth in claim 1, wherein the using amount of (i) C1–C4 hydrocarbons, (ii) carbon dioxide, and (iii) water vapor, in the feedstock mixture, and (iv) oxidant are (i) 22.94–38.17 vol %, (ii) 29.01–35.78 vol %, (iii) 9.54–17.65 vol %, and (iv) 20.35–23.85 vol %, respectively.

4. The process as set forth in claim 1, wherein the tri-reforming catalyst comprises 14.03–17.32 wt % Ni, 1.16–1.43 wt % Ce, 6.93–8.55 wt % $ZrO_2$, 16.36–20.20 wt % MgO, 20.05–24.75 wt % Cr, and 31.47–38.85 wt % $\gamma$-$Al_2O_3$.

5. The process as set forth in claim 1, wherein the binding material is any one selected from the group consisting of carbon black, graphite, pitch, and coal tar.

6. The process as set forth in claim 1, wherein the syngas comprises $H_2$ and CO at a volume ratio of 0.5–3.0:1.

7. The process as set forth in claim 1, wherein step (a) is performed at 900–1200° C.

8. The process as set forth in claim 1, wherein step (c) is performed at 150–400° C. under pressure of 20–350 kg/cm².

9. The process as set forth in claim 1, wherein the carbon dioxide separated in steps (b) and (d) is recovered, respectively, to be reused as feedstock in step (a).

* * * * *